United States Patent [19] [11] 3,974,152
Weir [45] Aug. 10, 1976

[54] 3-ETHYL- AND 3-(2'CYANOETHYL)-CEPHALOSPORINS

[75] Inventor: Niall Galbraith Weir, London, England

[73] Assignee: Glaxo Laboratories Limited, Greenford, England

[22] Filed: Nov. 19, 1973

[21] Appl. No.: 416,853

Related U.S. Application Data

[63] Continuation of Ser. No. 167,865, July 30, 1971, abandoned.

[30] Foreign Application Priority Data

Aug. 6, 1970 United Kingdom............... 38021/70

[52] U.S. Cl............................... 260/243 C; 424/246
[51] Int. Cl.$^2$......................... C07D 501/22
[58] Field of Search..................................... 260/243

[56] References Cited
UNITED STATES PATENTS 3,849,408  11/1974  Dolfini........................... 260/243 C
3,920,640  11/1975  Schorr et al. .................... 260/243 C
3,928,331  12/1975  Bauerschmidt et al. ......... 260/243 C Primary Examiner—Nicholas S. Rizzo
Assistant Examiner—Mary C. Vaughn
Attorney, Agent, or Firm—Bacon & Thomas

[57] ABSTRACT

New cephalosporin compounds are described characterized by possessing an ethyl group or a 2-cyanoethyl group as 3-position substituent. There is also described a method of preparing such compounds by reduction of a cephalosporin compound possessing the skeletal group $$3-CH=C<$$

11 Claims, No Drawings

3-ETHYL- AND 3-(2'CYANOETHYL)-CEPHALOSPORINS

This application is a continuation of application Ser. No. 167,865, filed on July 30, 1971, and now abandoned.

This invention is concerned with improvements in or relating to cephalosporin compounds.

The cephalosporin compounds referred to in this specification are generally named with reference to cepham, (see *J. Amer. Chem. Soc.* 1962, 84, 3400). The term "cephem" refers to the basic cepham structure with one double bond.

Where a dotted line bridges the 2-, 3- and 4- positions this indicates that the compound may be a ceph-2-em or a ceph-3-em compound.

As is well known in the art $\Delta^3$-4-carboxy cephalosporin antibiotics are compounds which are generally depicted by the formula

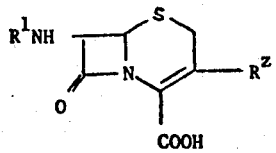

wherein $R^1$ is a carboxylic acyl group and $R^z$ is the 3-position substituent.

I have now found that compounds possessing the skeletal group

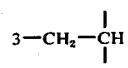

may be obtained by reduction of cephalosporin compounds containing a group of the type

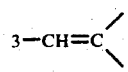

The resulting compounds are either useful antibiotics or are intermediates which are useful in preparing antibiotics.

Accordingly the invention provides a process for the preparation of compounds of the formula

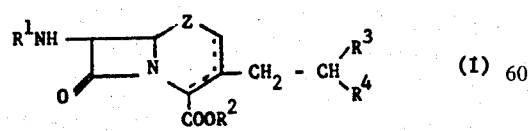

(wherein $R^1$ is a carboxylic acyl group; $R^2$ is hydrogen or a carboxyl-blocking group; $R^3$ and $R^4$, which may be the same or different, are each a hydrogen atom or an organic substituting group e.g. a lower alkyl group, an aryl (lower alkyl) group, an aryl group (e.g. phenyl or phenyl substituted by for example lower alkyl), a cycloalkyl group, a lower alkoxy crbonyl group, an aryl (lower alkoxy) carbonyl group, a diaryl (lower alkoxy) carbonyl group, a lower alkanoyl group, an aryloxycarbonyl group or a cyano group; and Z is >S or >S → O ($\alpha$ or $\beta$)) which comprises (A) reducing a compound of the formula

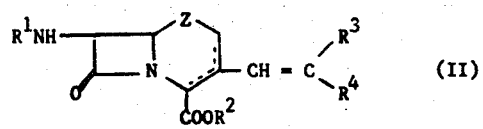

(wherein $R^1$, $R^2$, $R^3$, $R^4$ and Z have the above defined meanings) whereafter, if a compound of formula

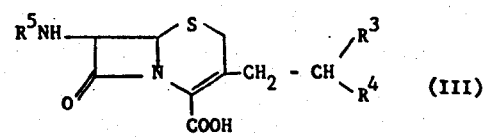

(wherein $R^5$ is a carboxylic acyl group which may be the same as $R^1$, and $R^3$ and $R^4$ have the above defined meanings) or a non-toxic derivative thereof is desired any of the following reactions (B) are carried out (i) conversion of a $\Delta^2$-isomer into the desired $\Delta^3$-isomer (ii) removal of any groups protecting any amino or carboxyl group (iii) reduction of a compound in which Z is >S → O to form the desired Z = >S compound and (iv) deacylation of a compound in which $R^5$ does not equal $R^1$ to form a 7-amino compound followed by reacylation to introduce the desired 7-$R^5$NH-group.

The invention will now be described in greater detail with reference to the cephalosporin starting materials, the reduction (A), subsequent reactions (B) and the products obtained.

CEPHALOSPORIN STARTING MATERIALS

Ceph-3-em-compounds of formula II may be prepared as described in Application No. 108136 (Clark et al), filed Jan. 20, 1971 by reaction of a 3-phosphoranylidenemethyl cephalosporin compound viz. a compound containing a 3-CH=PR$_3$ group (wherein R is an organic group) with a carbonyl compound of the formula $R^3 R^4$.CO ($R^3$ and $R^4$ having the above-defined meanings). The reaction with the carbonyl compound may be carried out by stirring the components together, e.g. at a temperature of from −30° to +100°C, if desired in an inert solvent.

Alternatively, where at least one of $R^3$ and $R^4$ is an electronegative group, compounds of formula II may be prepared as described in Application No. 108136, filed Jan. 20, 1971 by a reaction of a 3-formyl cephalosporin with a phosphorus ylid

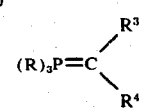

(where R, $R^3$ and $R^4$ have the above-defined meanings). The reaction with the phosphorus ylid may be carried out by stirring the compounds together at a temperature of from −80° to +100°C, if desired in an inert solvent.

A. REDUCTION

The reducton of the 3-vinyl or 3-substituted vinyl cephalosporin compound may be effected by any convenient method. The reduction should be so effected as not to cause any substantial saturation of the ceph-3-em or ceph-2-em system or reactions at the 7-position e.g. cleavage of the amido group. Reduction may cause simultaneous reduction of a 1-oxide group and/or cleavage of an ester group at the 4-position. These simultaneous reaction(s) need not be disadvantageous.

We have found that the reduction is conveniently achieved by hydrogenation promoted by a noble metal or compound thereof e.g. using palladized charcoal, e.g. at a temperature of from 10° to 40°C and e.g. at a pressure of up to 4 atmospheres. The promoter may be poisoned by the cephalosporin compound and prolonged times for the reaction and large amounts of the promoter may be required. An advantage of this method is that it can be effected withou saturation of the ceph-3-em or ceph-2-em systems.

The progress of the reduction may be followed chromatographically and by a shift of $\lambda_{max}$ to lower wavelengths in the ultraviolet because the conjugated chromophore is shortened.

Other reducing systems which may be employed include diimines; Zn/acetic acid; Zn/formic acid and metallohydrides (e.g. those derived from cobalt complexed in its lowest valencies).

compounds of formula II may exist in cis- and trans forms and where the isomers can be separated it may be found that one form is more readily hydrogenated than another. We have found, for example, that a cis-3-(2-cyanoethyl) compound is much more readily hydrogenated that its trans-isomer. It may therefore be desirable to effect isomerisation of the cephalosporin compound before hydrogenation e.g. by irradiation with ultraviolet light or γ-rays.

Protection of carboxyl groups

The group protecting the 4-carboxyl group may be formed with an alcohol (aliphatic or araliphatic), phenol, silanol, stannanol or acid which may readily be split off at a later stage of the reaction.

Suitable esters thus include compounds containing as 4-ester group, a group selected from the following list which is not intended to be an exhaustive list of possible ester groups i. COOCR$^a$R$^b$R$^c$ wherein at least one of R$^a$, R$^b$ and R$^c$ is an electron-donor e.g. p-methoxyphenyl, 2,4,6-trimethylphenyl, 9-anthryl, methoxy, acetoxy or fur-2-yl. The remaining R$^a$, R$^b$ and R$^c$ groups may be hydrogen or organic substituting groups. Suitable ester groups of this type include p-methoxy benzyloxycarbonyl and 2,4,6-trimethylbenzyloxycarbonyl.

ii. —COOCR$^a$R$^b$R$^c$ wherein at least one of R$^a$, R$^b$ and R$^c$ is an electron-attracting group e.g. benzoyl, p-nitrophenyl, 4-pyridyl, trichloromethyl, tribromomethyl, iodomethyl, cyanomethyl, ethoxycarbonylmethyl, arylsulphonylmethyl, 2-dimethylsulphoniumethyl, o-nitrophenyl or cyano. The remaining R$^a$, R$^b$ and R$^c$ groups may be hydrogen or organic substituting groups. Suitable esters of this type include benzoylmethoxycarbonyl, p-nitrobenzyloxycarbonyl, 4-pyridylmethoxycarbonyl, 2,2,2-trichloroethoxycarbonyl and 2,2,2-tribromoethoxycarbonyl.

iii. COOCR$^a$R$^b$R$^c$ wherein at least two of R$^a$, R$^b$ and R$^c$ are hydrocarbon such as alkyl e.g. methyl or ethyl, or aryl e.g. phenyl and the remaining R$^a$, R$^b$ and R$^c$ group, if there is one, is hydrogen. Suitable esters of this type include, t-butyloxycarbonyl, t-amyloxycarbonyl, diphenylmethoxycarbonyl and triphenylmethoxycarbonyl.

iv. COOR$^a$ wherein R$^a$ is adamantyl, 2-benzyloxyphenyl, 4-methylthiophenyl, tetrahydropyran-2-yl or tetrahydrofur-2-yl.

Silyl esters may conveniently be prepared from a halosilane or a silazane of the formula R$^4_3$SiX; R$^4_2$SiX$_2$; R$^4_3$Si.NR$^4_2$; R$^4_3$Si.NH.SiR$^4_3$; R$^4_3$Si.NH.COR$^4$; R$^4_3$Si.NH.CO.NH.SiR$^4_3$; R$^4$NH.CO.NR$^4$.SiR$^4_3$; or R$^4$C(OSiR$^4_3$):NSiR$^4_3$ where X is a halogen and the various groups R$^4$, which can be the same or different, represent hydrogen atoms or alkyl, e.g. methyl, ethyl, n-propyl, iso-propyl; aryl, e.g. phenyl; or aralkyl e.g. benzyl groups.

Preferred derivatives of silanols are silyl chlorides such as for example trimethylchlorosilane and dimethyldichlorosilane.

The carboxyl groups may be regenerated from an ester by any of the usual methods; for example, acid- and base-catalysed hydrolysis (especially for silyl and stannyl esters) is generally applicable, as well as enzymically-catalysed hydrolyses; however, aqueous mixtures may be poor solvents for these compounds and they may cause isomerizations, rearrangements, side-reactions, and general destruction, so that special methods may be desirable. Five suitable methods of deesterification are:

i. Reactions with Lewis acids: Suitable Lewis acids for reaction with the esters include trifluoroacetic acid, formic acid, hydrochloric acid in acetic acid, zinc bromide in benzene and aqueous solutions or suspensions of mercuric compounds. The reaction with the Lewis acid may be improved by addition of a nucleophile such as anisole. ii. Reduction: Suitable systems for effecting reduction are zinc/acetic acid, zinc/formic acid, zinc/lower alcohol, zinc/pyridine, palladised-charcoal and hydrogen, electrolysis, and sodium and liquid ammonia.

iii. Attack by nucleophiles: Suitable nucleophiles are those containing a nucleophilic oxygen or sulphur atom for example alcohols, mercaptans, thiocyanates and water.

iv. Oxidative methods: for example, those which involve the use of hydrogen peroxide and acetic acid.

v. Irradiation.

Protection of amino groups.

When the 7β-acylamido group contains an amino group it will be necessary to protect this during the various reaction stages. The protecting group is conveniently one which can be removed by hydrolysis without affecting the rest of the molecule, especially the lactam and 7β-amido linkages. The amine protecting group and the esterifying group at the 4-COOH position can be removed using the same reagent. An advantageous procedure is to remove both groups at the last stage in the sequence. Protected amine groups include urethane, arylmethyl (e.g. trityl) amino, arylmethyleneamino, sulphenylamino or enamine types. Such groups can in general be removed by one or more reagents selected from dilute mineral acids e.g. dilute hydrochloric acid, concentrated organic acids, e.g. concentrated acetic acid, trifluoroacetic acid, and liquid hydrogen bromide at very low temperature, e.g.

−80°C. A convenient protecting group is the t-butoxycarbonyl group, which is readily removed by hydrolysis with dilute mineral acid, e.g. dilute hydrochloric acid, or preferably with a strong acid (e.g. formic acid, trifluoroacetic acid or liquid HF) e.g. at a temperature of 0°–40°C., preferably at room temperature (15°–25°C). Another convenient protecting group is the 2,2,2-trichloroethoxycarbonyl group which may be split off by an agent such as zinc/acetic acid, zinc/formic acid, zinc/lower alcohols or zinc/pyridine. The $NH_2$ group may also be protected as $NH_3+$ by using the amino acid halide as its hydrohalide under conditions in which the amino group remains protonated.

Typical protecting groups and their methods of removal are illustrated in the following table:

acid, tetrahydrofuran, dioxan, dimethylformamide or dimethylacetamide. The reaction may be effected at a temperature of −20° to +50°C.

Alternatively, reduction of the 1-sulphinyl group may be effected by phosphorus trichloride or tribromide in solvents such as methylene chloride, dimethylformamide or tetrahydrofuran, preferably at a temperature of −20°C to +50°C.

An advantage associated with the use of a sulphoxide is that the compound will generally be a $\Delta^3$-compound.

Where the resultant compound is a ceph-2-em compound, the corresponding ceph-3-em compound may be obtained by treatment of the former with a base.

Removal of any groups protecting any amino or carboxyl groups may be effected as described above.

| Type | Example | Usual Name and Analogues etc. | Usual Method of Removal |
|---|---|---|---|
| Urethane | HNCOCH$_2$Ph $\parallel$ O | Benzyloxycarbonyl, p-Methoxy | HBr/AcOH (Neat) CF$_3$COOH (Neat) Liq. HBr at −80°C |
| Urethane | HNCOC(CH$_3$)$_3$ $\parallel$ O | t-Butoxycarbonyl | Dil. acid (HCl) CF$_3$COOH (Neat) |
| Urethane | HNCOCHPh$_2$ $\parallel$ O | Diphenylmethoxycarbonyl | CF$_3$COOH (Neat) Dil. HCl etc. |
| Urethane | HNCO—(1-adamantyl) $\parallel$ O | 1-Adamantyloxycarbonyl | Dil. HCl |
| Arylmethyl | HNCPh$_3$ | Trityl | AcOH + H$_2$O Dil. HCl |
| Sulphenyl | HN—S—C$_6$H$_4$—NO$_2$ | o-Nitrophenylsulphenyl, p-nitro- | Dil. HCl NaI or Na$_2$S$_2$O$_3$ pH 2–4 |
| Enamine | (β-dicarbonyl enamine structure with R group) | β-Dicarbonyl R=OEt Ethyl acetoacetate R=CH$_3$ Acetylacetone R=Ph Benzoylacetone R=OMe Methyl acetoacetate R=C$_2$H$_5$ Propionylacetone and many other β-diketones | Acid labile in varying degree Dil. AcOH or HCl etc. |
| Arylmethylene | N=CH—C$_6$H$_4$—OH | Anil (similar to β-dicarbonyl) from Salicylaldehyde 5-chlorosalicylaldehyde 3,5-dichlorosalicylaldehyde 2-hydroxy-1-naphthaldehyde 3-hydroxy-pyridine-4-aldehyde | Dil. HCl Formic acid |
| Onium Urethane | NH$_3^+$ $\mid$ HN.CO.OCH$_2$CCl$_3$ | β,β,β-trichloroethoxy-carbonyl | Base Reducing agents e.g. Zn/acetic acid |

B. SUBSEQUENT REACTIONS

Where the resultant compound contains a sulphinyl group at the 1-position this may be reduced by any convenient means. This may, for example, be effected by reduction of the corresponding acyloxysulphonium or alkyloxysulphonium salt prepared in situ by reaction with e.g. acetyl chloride in the case of an acetoxy-sulphonium salt reduction being effected by, for example, sodium dithionite or by iodide ion as in a solution of potassium iodide in a water miscible solvent e.g. acetic Where a resulting compound is a 7β-acylamido compound not having the desired acyl group, the 7β-acylamido compound may be N-deacylated to yield the corresponding 7β-amino compound and the latter acylated with an appropriate acylating reagent.

Suitable methods of N-deacylating cephalosporin derivatives having 7β-acylamido groups are described in British Pat. Nos. 1,041,985 and 1,119,806; Belgian Pat. No. 719,712 and in South African Pat. Specification Nos. 68/5048 and 68/5327. Another method of N-deacylation which may be used is acid catalysis. For example, N-deformylation of a 7β-formamido group may be effected with a mineral acid at a temperature of minus 15° to +100°C, preferably +15 to 40°C. N-Deformylation may be effected with the aid of a Lewis acid in a lower alkanol, preferably under substantially ahydrous conditions.

PRODUCTS OBTAINED

The resultant compounds of general formula (III) above include novel compounds e.g. were $R^3 = R^4 = H$. Such novel compounds have the general formula

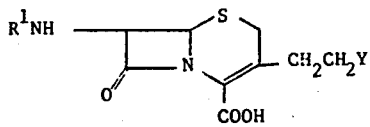

(wherein $R^1$ is a carboxylic acyl group and Y is hydrogen or a cyano group and non-toxic derivatives thereof) and constitute a further embodiment of the invention.

Compounds according to the invention possess antibacterial activity against a range of gram positive and gram negative organisms and are of value in human and veterinary medicine. They may also be of value in the preparation of other 3-substituted cephalosporin compounds.

Compounds of general formula (III) and non-toxic derivatives thereof, e.g. base salts (where applicable) and acid addition salts (where applicable), are antibiotics having interesting activity. We particularly prefer the compounds of formula (III) wherein $R^3 = R^4 = H$. By the term "non-toxic" as applied to the compounds of formula (III), we mean those derivatives which are physiologically acceptable in the dosage at which they are administered.

Salts which may be formed from the compounds according to the invention include (a) inorganic base salts such as alkali metal e.g. sodium and potassium, alkaline earth e.g. calcium, and organic base salts e.g. procain and dibenzylethylene diamine salts and (b) acid addition salts of any possible basic functions e.g. amino e.g. with hydrochloric, hydrobromic, sulphuric, nitric, phosphoric, toluene-p-sulphonic and methane-sulphonic acids. The salts may also be in the form of resinates, formed, e.g. with a polystyrene resin containing amino, quaternary amino, or sulphonic acid groups, or a resin containing carboxyl groups, e.g. a polyacylic acid resin. The resin may if desired be cross-linked, e.g. it may be a copolymer of styrene and divinylbenzene containing the appropriate groups.

An important series of compounds according to the invention are compounds of the general formula

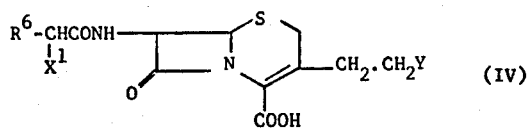

were $R^6$ is an aromatic group, e.g. phenyl or phenyl substituted with halo, hydroxy, lower alkyl, nitro, amino, lower alkanoyl, lower alkoxy or lower alkylmercapto, or a heterocyclic group (particularly a 5- or 6-membered heterocyclic group containing at least one hetero atom selected from S, N and O, e.g. thien-2-yl or thien-3-yl); $X^1$ is hydrogen, amino, substituted amino (e.g. acylamido), hydroxyl, substituted hydroxyl (e.g. acyloxy) or carboxyl; and Y is hydrogen or cyano; and non-toxic derivatives thereof.

Compounds of formula (IV) possess antibacterial activity against a range of gram positive and gram negative organisms and are of value in human and veterinary medicine.

The compounds of formula (IV) or salts thereof, may be used, where $X^1$ is not hydrogen, as a mixture of diastereoisomers or in one of the pure diastereoisomeric forms. Of particular interest are the compounds of the formula (IV) wherein the acid $R^6 CH(X^1)COOH$ is of the D- series. The derivatives of D(—) phenylglycine and the salts of those derivatives are of especial interest.

A particularly important compound of the general formula (IV) is 7β-(D-2-amino-2-phenylacetamido)-3-ethylceph-3-em-4-carboxylic acid of the formula:

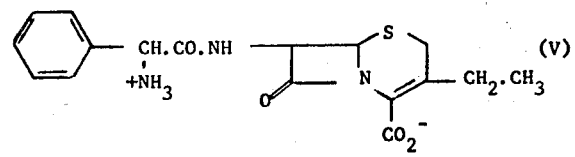

7β-(D-2-Amino-2-phenylacetamido)-3-ethylceph-3-em-4-carboxylic acid is a broad-spectrum antibiotic being active against gram-positive and gram-negative organisms as evidenced by in vitro tests. It is substantially resistant to degradation in vivo as evidenced by animal tests. A particularly significant property of this compound is that, when given by the oral route, it is well absorbed and gives good blood levels. It has an appreciable level of activity on oral administration. It will be appreciated that the property of absorption by the subject after oral administration is highly desirable.

An important series of compounds related to those of formula (V) are compounds of the formula:

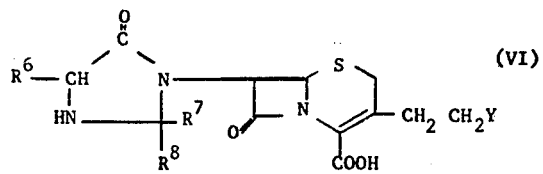

(where $R^7$ and $R^8$ which may be the same or different are lower akyl groups ($C_1 - C_4$), particularly methyl or ethyl, and $R^6$ and Y have the above defined meanings) and salts thereof. Such compounds may exist in isomeric forms (cf. J.Org.Chem. 1966, 31, 897).

The groups $R^1$ and $R^5$ in the above formulae may represent a wide variety of acyl groups which may contain 1–20 carbon atoms. Specific acyl groups are illustrated in the accompanying list which is not intended to be exhaustive:

i. R$^u$C$_n$H$_{2n}$CO- where R$^u$ is aryl (carbocyclic or heterocyclic), cycloalkyl, substituted aryl, substituted cycloalkyl, cyclohexadienyl, or a non-aromatic heterocyclic or mesoionic group, and n is an integer from 1–4. Examples of this group include phenylacetyl; substituted phenylacetyl e.g. fluorophenylacetyl, nitrophenylacetyl, aminophenylacetyl, acetoxyphenylacetyl, methoxyphenylacetyl, methylphenylacetyl, or hydroxyphenylacetyl; N,N-bis (2-chloroethyl) aminophenylpropionyl; thien-2- and 3-ylacetyl; 4-isoxazolyl and substituted 4-isoxazolylacetyl; pyridylacetyl; tetrazolylacetyl or a sydnoneacetyl group. The substituted 4-isoxazolyl group may be a 3-aryl-5-methyl isoxazol-4-yl group, the aryl group being e.g. phenyl or halophenyl e.g. chloro- or bromo- phenyl. An acyl group of this type is 3-o-chlorophenyl-5-methylisoxazol-4-ylacetyl.

ii. C$_n$H$_{2n+1}$CO— where n is an integer from 1–7. The alkyl group may be straight or branched and, if desired, may be inerrupted by an oxygen or sulphur atom or substituted by e.g. a cyano group, a carboxy group, an alkoxycarbonyl group, a hydroxy group or a carboxycarbonyl group (—CO.COOH). Examples of such groups include cyanoacetyl, hexanoyl, heptanoyl, octanoyl and butylthioacetyl.

iii. C$_n$H$_{2n-1}$CO—where n is an integer from 2–7. The alkenyl group may be straight or branched and, if desired, may be interrupted by an oxygen or a sulphur atom. An example of such a group is allylthioacetyl.

iv.

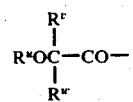

where R$^u$ has the meaning defined under (i) and in addition may be benzyl, and R$^v$ and R$^w$ which may be the same or different each represent hydrogen, phenyl, benzyl, phenethyl or lower alkyl. Examples of such groups include phenoxyacetyl, 2-phenoxy-2-phenylacetyl, benzyloxyacetyl, 2-phenoxypropionyl, 2-phenoxybutyryl, methylthiophenoxyacetyl.

v.

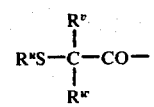

where R$^u$ has the meaning defined under (i) and, in addition, may be benzyl and R$^v$ and R$^w$ have the meanings defined under (iv). Examples of such groups include S-phenylthioacetyl, S-chlorophenylthioacetyl, S-fluorophenylthioacetyl, pyridylthioacetyl, and S-benzylthioacetyl.

vi. R$^u$Z (CH$_2$)$_m$CO— where R$^u$ has the meaning defined under (i) and, in addition, may be benzyl, Z is an oxygen or sulphur atom and m is an integer from 2–5. An example of such a group is S-benzylthiopropionyl.

vii. R$^u$CO— where R$^u$ has the meaning defined under (i). Examples of such groups include benzoyl, substituted benzoyl (e.g. aminobenzoyl), 4-isoxazolyl- and substituted 4-isoxazolylcarbonyl, cyclopentanecarbonyl, sydnonecarbonyl, naphthoyl and substituted naphthoyl (e.g. 2-ethoxynaphthoyl), quinoxalinylcarbonyl and substituted quinoxalinylcarbonyl (e.g. 3-carboxy-2-quinoxalinylcarbonyl). Other possible substituents for benzoyl include alkyl, alkoxy, phenyl, phenyl substituted by carboxy, alkylamido, cycloalkylamido, allylamido, phenyl(lower)alkylamido, morpholinocarbonyl, pyrrolidinocarbonyl, piperidinocarbonyl, tetrahydropyridino, furfurylamido or N-alkyl-N-anilino, or derivatives thereof, and such substituents may be in the 2- or 2- and 6- positions. Examples of such substituted benzoyl groups are 2,6-dimethoxybenzoyl, 2-methylamidobenzoyl and 2-carboxybenzoyl. Where the group R$^u$ represents a substituted 4-isoxazolyl group, the substituents may be as set out above under (i). Examples of such 4-isoxazolyl groups are 3-phenyl-5-methyl-isoxazol-4-yl carbonyl, 3-o-chlorophenyl-5-methyl-isoxazol-4-yl carbonyl and 3-(2,6-dichlorophenyl)-5-methyl-isoxazol-4-yl carbonyl.

viii.

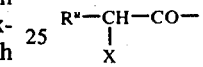

where R$^u$ has the meaning defined under (i) and X is amino, substituted amino (e.g. acylamido or a group obtained by reacting the α-aminoacylamido group of the 7-side chain with an aldehyde or ketone e.g. acetone, methylethylketone or ethyl acetoacetate), hydroxy, carboxy, esterified carboxy, azido, triazolyl, tetrazolyl, cyano, halogeno, acyloxy (e.g. formyloxy or lower alkanoyloxy) or etherified hydroxy group. Examples of such acyl groups are α-aminophenylacetyl, and α-carboxyphenylacetyl.

ix.

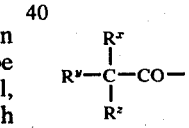

where R$^x$, R$^y$ and R$^z$ which may be the same or different may each represent lower alkyl, phenyl or substituted phenyl or R$^x$ represents hydrogen. An example of such an acyl group is triphenylmethylcarbonyl.

x. R$^u$—NH—CO— where R$^u$ has the meaning defined under (i) and in addition may be hydrogen, lower alkyl or halogen substituted lower alkyl. An example of such a group is Cl(CH$_2$)$_2$NHCO.

xi.

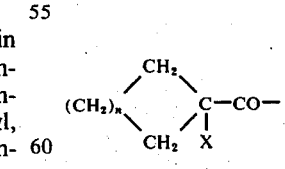

where X has the meaning defined under (viii) above and n is an integer of from 1 to 4. An example of such an acyl group is 1-aminocyclohexanecarbonyl.

xii. Amino acyl, for example R$^w$CH(NH$_2$).(CH$_2$)$_n$CO— where n is an integer from 1–10, or NH$_2$.C$_n$H$_{2n}$Ar(CH$_2$)$_m$CO, where m is zero or an integer from 1–10, and n is 0, 1 or 2, R$^w$ is a hydrogen atom or an alkyl, aralkyl or carboxy group or a group as defined under R" above, and Ar is an arylene group, e.g. p-phenylene or 1,4-naphthylene. Examples of such groups are disclosed in British Pat. Specification No. 1,054,806. A group of this type is the p-aminophenylacetyl group. Other acyl groups of this type include those, e.g. 5-aminoadipoyl, derived from naturally occurring amino acids, and derivatives thereof e.g. N-benzoyl-5-aminoadipoyl.

xiii. Substituted glyoxlyl groups of the formula $R''$.-CO.CO— where $R''$ is an aliphatic, araliphatic or aromatic group, e.g. a thienyl group, a phenyl group, or a mono-, di- or tri- substituted phenyl group, the substituents being, for example, one or more halogen atoms (F, Cl, Br, or I), methoxy groups, methyl groups or amino groups, or a fused benzene ring. Included in this group are also the α-carbonyl derivatives of the above substituted glyoxlyl groups.

xiv. Formyl.

Where compounds are primarily intended for use as intermediates, important species of the group $R^1$ are:

xv. Hydrocarbyloxycarbonyl and substituted hydrocarbyloxycarbonyl groups (wherein the 7-amino group forms part of a urethane), e.g. lower alkoxycarbonyl groups (such as methoxycarbonyl, ethoxycarbonyl and t-butoxycarbonyl groups); halo lower alkoxycarbonyl groups e.g. 2,2,2-trichloroethoxycarbonyl; aralkoxycarbonyl groups such as benzyloxycarbonyl, 4-methoxybenzyloxycarbonyl, diphenylmethoxycarbonyl and 4-nitrobenzyloxycarbonyl groups; and cycloalkoxycarbonyl groups e.g. adamantyloxycarbonyl.

xvi. Haloformyl e.g. chloroformyl.

The present invention also includes within its scope novel compounds of the general formula

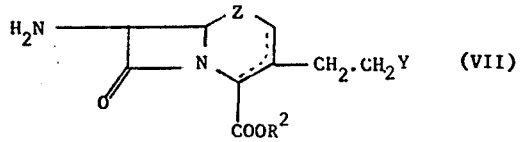

where Z, $R^2$, and Y have the above defined meanings and acid addition salts and base salts thereof. Acid addition salts include salts with hydrocarbyl sulphonic acids, e.g. p-toluene sulphonic acid, or nitric acid. .

Compounds of formula (VII) may be acylated to yield the desired compound of formula (III), if necessary employing a deesterification step.

Administration

The compounds according to the invention may be formulated for administration in any convenient way, by analogy with other antibiotics and the invention therefore includes within its scope a pharmaceutical composition comprising a compound of formula III or a non-toxic derivative e.g. salt thereof (as herein defined) adapted for use in human or veterinary medicine. Such compositions may be presented for use in conventional manner with the aid of any necessary pharmaceutical carriers or excipients.

The invention therefore provides pharmaceutical compositions comprising a compound of formula III or a non-toxic derivative thereof (as herein defined) in association with a pharmaceutical carrier or excipient. The compositions may be presented in a form suitable for absorption by the gastro-intestinal tract. Tablets and capsules for oral administration may be in unit dose presentation form, and may contain conventional excipients such as binding agents, for example syrup, acacia, gelatin, sorbitol, tragacanth, or polyvinylpyrrolidone; fillers, for example, lactose, sugar, maize-starch, calcium phosphate, sorbitol or glycine; lubricants, for example, magnesium stearate, talc, polyethylene glycol, silica; disintegrants, for example, potato starch or acceptable wetting agents such as sodium lauryl sulphate. The tablets may be coated according to methods well known in the art. Oral liquid preparations may be in the form of aqueous or oily suspensions, solutions, emulsions, syrups, elixirs, etc. or may be presented as a dry product, for reconstitution with water or other suitable vehicle before use. Such liquid preparations may contain conventional additives such as suspending agents, for example, sorbitol syrup, methyl cellulose, glucose/sugar syrup, gelatin, hydroxyethylcellulose, carboxymethyl cellulose, aluminium stearate gel or hydrogenated edible fats; emulsifying agents, for example, lecithin, sorbitan mono-oleate or acacia; non-aqueous vehicles which may include edible oils, for example, almond oil, fractionated coconut oil, oily esters, propylene glycol, or ethyl alcohol; preservatives, for example, methyl or propyl p-hydroxybenzoates or sorbic acid. Suppositories will contain conventional suppository bases, e.g. cocoa butter or other glyceride.

Compositions for injection may be presented in unit dose form in ampoules, or in multidose containers with an added preservative. The compositions may take such forms as suspensions, solutions, emulsions in oily or aqueous vehicles, and may contain formulatory agents such as suspending, stabilising and/or dispersing agents. Alternatively the active ingredient may be in powder form for reconstitution with a suitable vehicle, e.g. sterile, pyrogen-free water, before use.

The compositions may also be prepared in suitable forms for absorption through the mucous membranes of the nose and throat or bronchial tissues and may conveniently take the form of powder or liquid sprays or inhalants, lozenges, throat paints etc. For medication of the eyes or ears, the preparations may be presented as individual capsules, in liquid or semi-solid form, or may be used as drops etc. Topical applications may be formulated in hydrophobic or hydrophilic bases as ointments, creams, lotions, paints, powders etc.

For veterinary medicine the composition, may, for example, be formulated as an intramammary preparation in either long acting or quick-release bases.

The compositions may contain from 0.1% upwards, preferably from 10–99% of the active material, depending on the method of administration. Where the compositions comprise dosage units, each unit will preferably contain 50–500 mg. of the active ingredient. The dosage as employed for adult human treatment will preferably range from 100–3000 mg. for instance 1500 mg. per day, depending on the route and frequency of administration.

The compounds according to the invention may be administered in combination with other therapeutic agents such as antibiotics, for example other cephalosporins, the penicillins or tetracyclines.

In order that the invention may be well understood the following Examples are given by way of illustration only.

In the Examples, unless otherwise stated
1. Optical rotations were determined at 19° to 30°.

2. Solutions were dried over anhydrous magnesium sulphate.

3. All grades of Kieselgel were supplied by Merck AG Dermstadt, Germany.

4. Proton magnetic resonance (PMR) spectra were determined at 60 or 100 MHz. The signs of the coupling constants (J) are not assigned. Signals are assigned as singlets (s) doublets (d), double doublets (dd), triplets (t), quarters(q), double quartets (dq), AB-quartets (AB-q), quintets (qu) and multiplets (m)

System B is n-butanol:ethanol:water = 4:1:5, equilibrated at room temperature, the upper phase being used as developer in descending manner, in equilibrium with lower phase, on Whatman No. 1 paper buffered to pH 6 with 0.05M sodium dihydrogen phosphate.

System C is ethyl acetate: n-butanol: 0.1M-sodium acetate pH 5 = 8:1:8, equilibrated at 38°C, the upper phase being used as developer in descending manner, in equilibrium with lower phase at 38°, on No. 1 Whatman paper buffered to pH 5 with 0.1M sodium acetate.

Light petroleum was the fraction, b.p. 40° to 60°. Methylene chloride was dried on Woelm Grade I basic alumina. Thin-layer chromatography was carried out upwards on Merck silica plates.

As far as possible, analytical values for solvates were confirmed by the inspection for the appropriate features in the spectra.

$R_P$ represents the $R_F$ value divided by that of 3-acetoxymethyl-7$\beta$-(phenylacetamido) ceph-3-em-4-carboxylic acid.

EXAMPLE 1 a. Diphenylmethyl 3-Ethyl-7$\beta$-(2-thienylacetamido)ceph-3-em-4-carboxylate.

Hydrogen was bubbled through a suspension of 10%-palladium on carbon (12.77g., 0.012 g. atoms) in pure tetrahydrofuran (500 ml.) for 15 minutes. A solution of diphenylmethyl 7$\beta$-(2-thienylacetamido)-3- vinylceph-3-em-4-carboxylate (5.02 g., 9.7 m.moles) in pure tetrahydrofuran (250 ml.) was added and the mixture stirred vigorously in a hydrogen stream for 45 minutes. The system was flushed with nitrogen and the catalyst removed by filtration of the suspension through a bed of kieselguhr. The filtrate was evaporated in vacuo and the residue (4.99 g.) crystallised from methanol to give the title compound (3.11 g., 62%) as needles, m.p. 135° to 137°, $[\alpha]_D^{22}$ + 32.8° (c 1.0 CHCl$_3$), $\lambda_{inflex}$. (EtOH) 256 nm ($\epsilon$ 6,850), $\nu_{max}$. (CHBr$_3$) 3420 (NH), 1782 ($\beta$-lactam), 1722 (CO$_2$R), and 1690 and 1515 cm.$^{-1}$ (CONH), $\tau$ (CDCl$_3$) 3.46 (NH, d, J9 Hz.), 4.3 (C$_{(7)}$-H, dd, J 9 and 4.5 Hz.), 5.1 (C$_{(6)}$-H, d, J 4.5 Hz.), 6.19 (CH$_2$CO), 6.65 and 6.76 (C$_{(2)}$-CH$_2$, AB-q, J 18 Hz.), 7.49 and 7.8 (—CH$_2$CH$_3$, 2 pairs of q, ABX$_3$-system, $J_{AX}$=$J_{BX}$ 7, and $J_{AB}$ 13 Hz.), and 8.98 (CH$_2$—CH$_3$, t, J 7 Hz.) (Found: C, 65.2; H, 5.1; N, 5.0; S, 12.4. C$_{28}$H$_{26}$N$_2$O$_4$S$_2$ requires C, 64.9; H, 5.05; N, 5.4; S, 12.35%.

b. Diphenylmethyl 7$\beta$-Amino-3-ethylceph-3-em-4-carboxylate.

A suspension of phosphorus pentachloride (2.02 g., 9.65 m.moles) in methylene dichloride (15 ml.) was stirred at 16° for ca 10 minutes (solution nearly complete). A solution of dry pyridine (763 mg. 9.65 m.moles) in methylene dichloride (11.5 ml.) was added over a 5-minute period and the resulting suspension warmed to 25° for 10 minutes. After the mixture had been cooled to 16° a solution of diphenylmethyl 3-ethyl-7$\beta$-(2-thienylacetamido)ceph-3-em-4-carboxylate (2.23 g., 4.3 m.moles) in methylene dichloride (20 ml.) was added and the orange solution stirred at 16° for 2½ hours. The mixture was run slowly (over 15 minutes) into a vigorously stirred solution of methanol (3 ml.) in methylene dichloride (12 ml.). The resulting solution was stirred with an excess of saturated aqueous sodium bicarbonate solution until the pH of the aqueous phase remained > 7. The organic layer was separated and washed with water, and dried and evaporated in vacuo. Benzene was distilled off the residue to remove traces of pyridine as an azeotrope, and the resulting gum was triturated with ether to give the 7-aminoester (1.16 g., 67%) as a cream solid, m.p. 141° to 142° (decomp.), $[\alpha]_D^{22}$ + 4.2° (c 1.0, CHCl$_3$),$\lambda_{max}$. (EtOH) 264 to 268 nm. ($\epsilon$ 5,680), $\nu_{max}$.(Nujol) 3420 and 3350 (NH$_2$), 1760 ($\beta$-lactam) and 1720 cm.$^{-1}$ (CO$_2$R), $\tau$ (DMSO-d$^6$) 3.04 (CH Ph$_2$), 5.00 (C$_{(7)}$—H, d, J 4.5 Hz.), 5.19 (C$_{(6)}$-H, d, J 4.5 Hz.), 6.37 and 6.61 (c$_{(2)}$-CH$_2$, AB-q, J 18 Hz.), ca 7.7 (-CH$_2$CH$_3$, complex partly obscured by DMSO-bands), and 9.00 (-CH$_2$CH$_3$, t, J 7 Hz.) (Found: C, 65.7; H, 5.6; N, 6.8; S, 8.4. C$_{22}$H$_{22}$N$_2$O$_3$S.½H$_2$O requires C, 65.3; H, 6.0; N, 6.9; S, 7.9%).

c. Diphenylmethyl 7$\beta$-(D-2-t-Butoxycarbonylamino-2-phenylacetamido)-3-ethylceph-3-em-4-carboxylate.

A solution of diphenylmethyl 7$\beta$-amino-3-ethylceph-3-em-4-carboxylate (1g., 2.53 m.moles) in methylene dichloride (14.5 ml.) with dicyclohexylcarbodiimide (521 mg., 2.55 m.moles) was treated slowly (over 10 minutes) with a solution of D-2-t-butoxycarbonylamino-2-phenylacetic acid (640 mg., 2.55 m.moles) in N,N-dimethylformamide (13 ml.). The mixture was stirred vigorously at 20° for 1.75 hours, and then kept at 5° for 18 hours. Precipitated dicyclohexylurea was removed by filtration, and the filtrate evaporated in vacuo. The residue was taken up in benzene-ethyl acetate (4:1) (some more dicyclohexylurea was removed by filtration) and chromatographed on Merck Kieselgel (0.05 to 0.2 mm., 40 g., ). Fractions containing material with similar mobilities on tlc (R$_f$ ca. 0.8; benzene: ethyl acetate = 3:1) were combined and evaporated in vacuo. The residue, in ethyl acetate, was run into petroleum ether (b.p. 40° to 60°) to give the title compound (1.06 g., 66.7%) as an amorphous solid, m.p. 123 to 125° (decomp.), $[\alpha]_D^{22}$ – 16.5° (c 0.97, CHCl$_3$), $\lambda_{max}$.(EtOH) 263.5 nm. ($\epsilon$ 6,400), $\nu_{max}$.(CHBr$_3$) 3470 (NH), 1790 ($\beta$-lactam), 1725 (CO$_2$R), and 1700 and 1500 cm.$^{-1}$ (CONH), $\tau$ (CDCl$_3$) 3.11 (CH Ph$_2$), 3.3 (CONH, d, J 9 Hz.), 4.30 (NH CH, d, J 7 Hz.), 4.31 (C$_{(7)}$-H, dd, J 4.5 and 9 Hz.), 4.81 (NHCH, d, J 7 Hz.) 5.13 (C$_{(6)}$—H, d, J 4.5 Hz.), 6.71 and 6.93 (C$_{(2)}$—CH$_2$, AB-q, J 18 Hz.) ca 7.56 and 7.76 (CH$_2$CH$_3$, 2 pairs of q; ABX$_3$-system, J$_{AX}$=J$_{BX}$ 7, and J$_{AB}$ 13 Hz), 8.6 (C[CH$_3$]$_3$), and 9.01 (CH$_2$CH$_3$, t, J 7 Hz) (Found: C, 66.8; H, 6.2; N, 6.5; S, 4.9. C$_{35}$H$_{37}$N$_3$O$_6$S requires C, 67.0; H, 5.95; N, 6.7; S, 5.1%).

d. 7$\beta$-(D-2-Amino-2-phenylacetamido)-3-ethylceph-3-em-4-carboxylic acid, Trifluoroacetic Acid Salt.

Diphenylmethyl 7$\beta$-(D-2-t-butoxycarbonylamino-2-phenylacetamido)-3-ethylceph-3-em-4-carboxylate (936 mg.) with anisole (0.95 ml.) was treated with trifluoroacetic acid (3.8 ml.). After 5 minutes at 23° the solvents were removed in vacuo, and the residue partitioned between water (containing some trifluoroacetic acid) and ethyl acetate. The ethyl acetate solution was extracted with further amounts of dilute trifluoroacetic acid and the aqueous solutions combined. After removal of traces of ethyl acetate from the aqueous phase in vacuo the solution was freeze-dried to give the title compound (560 mg., 79% after drying in vacuo over phosphorus pentoxide) as an amorphous solid, m.p. ca 150° (decomp.), $[\alpha]_D^{22}$ + 69.4° (C 1.0, 1% NaHCO$_3$), $\lambda_{max}$. (0.1 M-pH 6 phosphate buffer) 261 nm. ($\epsilon$ 7,350), $\nu_{max}$. (Nujol) 1760 ($\beta$-lactam), 1675 and 1530 (CONH) and 1670 cm.$^{-1}$ (CF$_3$CO$_2$-), $\tau$ (DMSO-d$^6$) 0.46 (NH, d, J 9 Hz.), 1.2 ($^+$NH$_3$ very broad), 2.52(Ph), 4.32 (C$_{(7)}$—H, dd, J 9 and 4.5 Hz.), 4.93 (CH-NH), 5.00 (C$_{(6)}$—H, d, J 4.5 Hz.), 6.47 and 6.72 (C$_{(2)}$—CH$_2$, AB-q, J 18 Hz.), 7.5 to 7.9 (CH$_2$ CH$_3$, AB-part of ABX$_3$-system partly obscured by DMSO bands), and 8.96 (CH$_2$CH$_3$, t, J 7 Hz.) (Found: C, 45.9; H, 4.2; F, 11.7; N, 8.6; S, 6.4. C$_{19}$H$_{20}$F$_3$N$_3$O$_6$S. H$_2$O requires C, 46.3; H, 4.5; F, 11.6; N, 8.5; S, 6.5%).

EXAMPLE 2 a. Diphenylmethyl 3-(cis-2-Cyanovinyl)-7$\beta$-(2thienylacetamido)ceph-3-em-4-carboxylate A solution of cyanomethylenetriphenylphosphorane (3.77 g., 12.5 mmoles) in dry methylene chloride (45 ml.) at −20° was added slowly (over ca. 20 minutes) to a solution of diphenylmethyl 3-formyl-7$\beta$-(2-thienylacetamido) ceph-3-em-4-carboxylate (6.48 g., 12.5 mmoles) at −20°. After 40 minutes at −20° the solution was washed with N-hydrochloric acid (45 ml.) and water, and dried and evaporated in vacuo. The residue, in benzene - ethyl acetate (8:1), was chromatographed on Merck Kieselgel (0.02 – 0.5 mm., 380 g.). Fractions containing material with similar mobilities on T.L.C. (R$_F$ ca 0.6) were combined and evaporated in vacuo. The residue (2.76 g., 40%) was crystallised from acetone - light petroleum to give the cis-cyano vinyl compound (2.26 g., 33%) as fine needles, m.p. 171.5°–172.5° (decomp.), $[\alpha]_D^{23}$ − 258° (c 1.0, CHCl$_3$), $\lambda_{max}$. (EtOH) 318 nm. ($\epsilon$ 17,700), $\nu_{max}$. (CHBr$_3$) 3415 (NH), 2230 (CN), 1796 ($\beta$-lactam), 1728 (CO$_2$R) and 1690 and 1512 cm.$^{-1}$ (CONH), $\tau$ (CDCl$_3$) 2.9 and 4.8 (CH=CH, two d, J 12 Hz.), 3.44 (NH, d, J 9 Hz.), 4.1 (C$_{(7)}$-H, dd, J 4.5 and 9 Hz.), 5.02 (C$_{(6)}$—H, d, J 9 Hz.), 5.89 and 6.29 (C$_{(2)}$—CH$_2$, AB-q, J 18 Hz.), 6.19 (CH$_2$CONH, singlet) (Found: C, 64.2; H, 4.4; N, 7.5; S, 11.5. C$_{29}$H$_{23}$N$_3$O$_4$S$_2$ requires C, 64.3; H, 4.3; N, 7.75; S, 11.85%).

b. Diphenylmethyl 3-(2-Cyanoethyl)-7$\beta$-(2thienylacetamido)ceph-3-em-4-carboxylate Hydrogen was bubbled through a suspension of 10%-palladium on carbon (9.59 g., 0.009 g. atoms) in pure tetrahydrofuran (100 ml.) for 15 minutes. A solution of diphenylmethyl 3-(2-cis-cyanovinyl)-7$\beta$-(2-thienylacetamido) ceph-3-em-4-carboxylate (4.068 g., 7.5 m.moles) in pure tetrahydrofuran (100 ml.), which had been saturated with hydrogen, was added and the mixture stirred vigorously in a hydrogen stream for 4 hours. The system was flushed with nitrogen and the catalyst removed by filtration of the suspension through a bed of kieselguhr. The filtrate was evaporated in vacuo to give a crude produce which still contained substantial amounts of the starting vinyl compound. The above process was repeated using the crude material and 10%-palladium on carbon (12.75 g., 0.012 g. atoms), but in this case the vinyl compound in tetrahydrofuran was added slowly to the catalyst suspension and the total reaction time was increased to 8½ hours. The product thus obtained (ca 3.8 g.), in chloroform, was chromatographed on Merck Kieselgel (0.05 to 0.2 mm., 100 g) with chloroform and chloroform-ethyl acetate (8:1) for elution. Fractions containing material with similar mobilities on tlc (R$_F$ca. 0.5 and 0.4 using benzene:ethyl acetate = 8:1) were the starting cis-cyanovinyl compound (300 mg.) and the crude cyanoethyl compound respectively. The latter material was further purified by chromatography (as above), followed by crystallisation from chloroform, to give rods of the pure cyanoethyl compound (1.87 g., 46%), as a solvate, m.p. ca. 97° (decomp., then partially solidifying and remelting at ca 163°), $[\alpha]_D^{23}$ + 3.2° (C 1.0, DMSO), $\nu_{max}$. (Nujol) 3360 and 3270 (NH), 1790 ($\beta$-lactam), 1730 (CO$_2$R), 1662 and 1522 (CONH), and 695 cm.$^{-1}$ (phenyl), $\tau$ (pyridine -d$^5$) 1.58 (probably CHCl$_3$), 3.7 (C$_{(7)}$—H, dd, J 4,5 and 9 Hz.) 4.81 (C$_{(6)}$—H, d, J 4.5 Hz), 5.94 (CH$_2$—CONH), 6.43 (C$_{(2)}$—CH$_2$), and 7.1 to 7.6 (CH$_2$CH$_2$CN, ABCD-complex) (Found: C, 59.65; H, 4.35; Cl, 6.1; N, 6.9; S, 10.6. C$_{29}$H$_{25}$N$_3$O4S$_2$, 0.35 CHCl$_3$ requires C, 60.2; H, 4.35; Cl, 6.35; N, 7.15; S, 10.95%).

c. 3-(2-Cyanoethyl)-7$\beta$-(2-thienylacetamido)ceph-3-em-4-carboxylic acid.

A solution of diphenylmethyl 3-(2-cyanoethyl)-7$\beta$-(2-thienylacetamido)ceph-3-em-4-carboxylate (1g.) in anisole (1 ml.) was treated with trifluoroacetic acid (4 ml.). After 5 minutes at 23° the solvents were removed in vacuo and the residue was partitioned between ethyl acetate and dilute aqueous sodium bicarbonate solution. The alkaline phase was washed thoroughly with ethyl acetate, then taken to pH2 with 2N-hydrochloric acid. The acidic mixture was extracted with ethyl acetate and the organic extracts washed with brine, and dried and evaporated in vacuo. The residual gum was dissolved in ethyl acetate and the solution run into petroleum ether to give, after filtration and drying, the title acid (567 mg., 82%) as an amorphous solid, m.p. ca 105° (decomp.) $[\alpha]_D^{22}$ + 102° (C 0.75, 1% NaHCO$_3$), $\lambda_{inflex}$.(0.1 M-pH 6 phosphate buffer) 260 nm. ($\epsilon$ 7,290), $\nu_{max}$.(Nujol) 3300 (NH), 3675 to 2400 (bonded OH), 2210 and 2250 (CN), 1775 ($\beta$-lactam), 1715 (CO$_2$H), and 1665 and 1530 cm.$^{-1}$ (CONH), $\tau$ (D$_2$O with NaHCO$_3$) 4.43 (C$_{(7)}$—H, d, J 4.5 Hz), 4.95 (C$_{(6)}$—H, d, J 4.5 Hz.), 6.13 (CH$_2$CONH), 6.42 and 6.82 (C$_{(2)}$, AB-q, J 18 Hz.), and 7.1 to 7.6 (CH$_2$CH$_2$CN, ABCD-complex) (Found: C, 50.7; H, 4.0; N, 10.7; S, 16.0; C$_{16}$H$_{15}$N$_3$O$_4$S$_2$ requires C, 50.9; H, 4.0; N, 11.1; S, 17.0%), R$_f$0.28 (System C) and R$_f$ 0.6 (System B).

EXAMPLE 3

3-Ethyl-7$\beta$-(2-thienylacetamido)ceph-3-em-4-carboxylic acid

Diphenylmethyl 3-ethyl-7$\beta$-(2-thienylacetamido)-ceph-3-em-4-carboxylate (1.0 g.) was treated with anisole (1 ml.) and trifluoroacetic acid (4 ml.). After 4 minutes at ca. 22° the solvents were removed in vacuo and the residue dissolved in ethyl acetate, and the solvent again removed in vacuo. The residue was dissolved in ethyl acetate and the resulting solution run into petroleum ether (b.p. 40 to 60°) over 6 minutes. Filtration gave the acid (6.70 mg.) as an amorphous solid, m.p. 148° to 153° (decomp.), $[\alpha]_D^{22} + 146.8°$ (c 1.0, 1% NaHCO$_3$), $\lambda$ inflexion (0.1 M-pH 6 phosphate buffer) at 260 nm. ($\epsilon$ 7,925), $\nu_{max.}$ (Nujol) 3265 (NH), 1754 ($\beta$-lactam), 1696 and 2650 (CO$_2$H) and 1652 and 1540 cm.$^{-1}$ (CONH), $\tau$ (D$_2$O with NaHCO$_3$) 2.76 and 3.06 (thienyl), 4.52 (C$_{(7)}$—H, d, J 4.5 Hz.), 5.03 (C$_{(6)}$—H, d, J 4.5 Hz.), 6.17 (CH$_2$CO), 6.52 and 6.87 (C$_{(2)}$—CH$_2$, AB-q, J 18 Hz.), 7.74 (CH$_2$CH$_3$, m; ABX$_3$-system), and 8.98 (CH$_2$CH$_3$, t) (Found: C, 52.5; H, 4.8; N, 7.2; S, 17.1. C$_{15}$H$_{16}$N$_2$O$_4$S$_2$ requires C, 51.1; H, 4.6; N, 7.95; S, 18.2%). R$_f$ 0.55 (System C).

EXAMPLE 4 a. Diphenylmethyl 7$\beta$-(D-2-t-butoxycarbonylamino-2-phenylacetamido)-3-ethylceph-3-em-4-carboxylate Hydrogen was bubbled through a suspension of 10% palladium on carbon (27.5 g., 0.026 g. atoms) in pure tetrahydrofuran (850 ml.) for 30 minutes. A solution of diphenylmethyl 7$\beta$-(D-2-t-butoxycarbonylamino-2-phenylacetamido)-3-vinylceph-3-em-4-carboxylate [12.03 g., 19.2 m. moles prepared as described in the Appendix below] in pure tetrahydrofuran (450 ml.) was added in four aliquots, over a 30-minute period, and the mixture stirred vigorously in a hydrogen stream for 1¼ hours. The system was flushed with nitrogen and the catalyst removed by filtration of the suspension through a bed of kieselguhr. The solvent was removed in vacuo and the residue dissolved in benzene: ethyl acetate = 2:1, and the solution filtered through a short column of Merck Kieselgel (0.05–0.2 mm., 7.5 × 4 cm.). The column was washed thoroughly with benzene : ethyl acetate = 2:1 and the combined washings evaporated in vacuo. Crystallisation of the residue from ether gave the ethyl compound (7.96 g., 66%) as fine needles, m.p. 138 to 139°, $[\alpha]_D^{22}$ - 15.7° (c 0.9, CHCl$_3$), $\lambda_{max.}$ (EtOH) 264 mm. ($\epsilon$5,700), $\nu_{max.}$ (CHBr$_3$) 3470 (NH), 1790 ($\beta$-lactam), 1725 (CO$_2$R), and 1700 and 1500 cm.$^{-1}$ (CONH), $\tau$ (CDCl$_3$) 3.06 (CHPh$_2$), 3.18 (CONH, d J 9 Hz.), 4.26 (CHNH, d, J 7 Hz.), 4.3 (C$_{(7)}$—H, dd, J 4.5 and 9 Hz.), 4.76 (NHCH, d, J 7 Hz.), 5.12 (C$_{(6)}$—H, d, J 4.5 Hz.), 6.71 and 6.93 (C$_{(2)}$—CH$_2$, AB-q, J 18 Hz.), 7.48 =J7.84 (CH$_2$CH$_3$, 2 pairs of q, ABX$_3$—system, J$_{AXBX}$ 7, and J$_{AB}$ 13 Hz.), 8.6 (C[CH$_3$]$_3$), and 9.01 (CH$_2$CH$_3$, t, J 7 Hz.) (Found: C, 67.1; H, 6.1; N, 6.5; S, 5.0. C$_{35}$H$_{37}$N$_3$O$_6$S requires C, 67.0; H, 5.95; N, 6.7; S, 5.1%). A second crop of the title compound (518 mg.), m.p. 133° to 135°, $[\alpha]_D^{22}$ - 12.9° (c 1.0, CHCl$_3$) was also obtained.

b. 7$\beta$-(D-2-Amino-2-phenylacetamido)-3-ethylceph-3-em-4-carboxylic acid

Diphenylmethyl 7$\beta$-(D-2-t-butoxycarbonylamino-2-phenylacetamido)-3-ethylceph-3-em-4-carboxylate (.8 g.) with anisole (8 ml.) was treated with trifluoroacetic acid (32 ml.). After 5 minutes at 23° the solvents were removed in vacuo, and the residue partitioned between water (containing some trifluoroacetic acid) and diethyl ether. After removal of traces of diethyl ether from the aqueous phase in vacuo the solution was freeze-dried to give the trifluoroacetic acid salt of the title compound (5.75 g., 95%). This material in water (ca 40 ml.) was taken to pH 5 with 50% aqueous ammonium hydroxide. Filtration gave the title compound (3.9 g., 84.5%) as small prisms, m.p. 180° (vigorous decomp.), $[\alpha]_D^{23} + 100°$ (C 0.9, 1% NaHCO$_3$), $\lambda_{max.}$ (0.1 M- pH 6 phosphate buffer) 262 nm. ($\epsilon$ 7,700), $\lambda_{max.}$(Nujol) 3360 (NH), ca 2700 (NH$_3$+), 1776 ($\beta$-lactam), and 1700 and 1510 cm.$^{-1}$(CONH), $\tau$ (CF$_3$CO$_2$H) ca. 2.2 (NH$_3$+), 2.42(Ph), 4.26 (C$_{(7)}$-H, d, J 4.5 and 9 Hz.), 4.44 (CH NH$_3$+, q), 4.81 (C$_{(6)}$-H, dd, J 4.5 Hz.), 6.49 and 6.69 (C$_{(2)}$—$_{CH2}$, AB-q J 18 Hz.), 7.09 and 7.47 (CH$_2$CH$_3$, 2 pairs of q; ABX$_3$-system J$_{AX}$ = J$_{BX}$ 7, and J$_{AB}$ 13 Hz.) and 8.8 (CH$_2$CH$_3$, t) (Found: C, 53.1; H, 5.2; N, 11.0; S, 8.7. C$_{17}$H$_{19}$N$_3$O$_4$S. 1¼ H$_2$O requires C, 53.2; H, 5.6; N, 10.95; S, 8.35. An anhydrous product could not be obtained after prolonged drying in vacuo at 65°.

EXAMPLE 5 a. t-Butyl 3-Ethyl-7$\beta$-phenoxyacetamidoceph-3-em-4-carboxylate

Hydrogen was bubbled through a suspension of 10%-palladium on carbon (3 g, 0.00282 g atoms) in dry ethyl acetate (100 ml.) for 30 minutes. A solution of t-butyl 7$\beta$-phenoxyacetamido-3-vinylceph-3-em-4-carboxylate (1.4 g., 3.36 mmole) in dry ethyl acetate (50 ml.) was added and the mixture was stirred for 2½ hours in a hydrogen stream and filtered through a bed of kieselguhr. The filtrate was evaporated in vacuo to give the title ester as a white foam (1.21 g, 86.5%), $[\alpha]_D^{23} + 55.4°$ (c 0.85; CHCl$_3$), $\lambda_{max.}$ (EtOH) 263 nm($\epsilon$ 8,100) and 268 nm ($\epsilon$ 8,450), inflexion at 273 nm ($\epsilon$ 7,600), $\nu_{max.}$(CHBr$_3$) 3420(NH), 1782 (azetidin-2-one), 1715 (CO$_2$R), and 1695 and 1525 cm.$^{-1}$ (CONH), $\tau$ (CDCl$_3$) 2.66 and 3.03 (2H and 3H, two m; C$_6$H$_5$O) 4.15 (1H, dd, J 9.5 and 5 Hz; C$_7$—H), 5.00 (1H, d, J 5 Hz; C$_6$—H) 5.45 (2H, s; C$_6$H$_5$OCH$_2$), 6.51 and 6.73 (2H, AB-q, J 18 Hz; C$_2$—H$_2$), 7.37 and 7.80 (2H, AB-part of ABX$_3$-system, J$_{AX}$, J$_{BX}$ 7 Hz, J$_{AB}$ 13 Hz; C$_3$—CH$_2$CH$_3$), 8.47 (9 H, s; CO$_2$C(CH$_3$)$_3$), 8.87 (3 H, t, J 7 Hz; CH$_2$CH$_3$) (Found: C, 60.1; H, 6.3; N, 6.7; S, 7.2. C$_{21}$H$_{26}$N$_2$O$_5$S (418.5) requires C, 60.25; H, 6.2; N, 6.8; S, 7.7%).

b. 3-Ethyl-7$\beta$-phenoxyacetamidoceph-3-em-4-carboxylic acid

Trifluoroacetic acid (12 ml.) was added to a stirred solution of t-butyl 3-ethyl-7$\beta$-phenoxyacetamidoceph-3-em-4-carboxylate (1.255 g, 3 mmole) in anisole (3 ml.) at 22°. The solution was stirred for 10 minutes and the solvents were removed in vacuo. The residual oil was dissolved in ethyl acetate (60 ml.) and the solution was extracted with 3% aqueous sodium hydrogen carbonate solution (2 × 10 ml.). The combined extract was washed with ethyl acetate (60 ml.), acidified to pH 2.5 with concentrated hydrochloric acid and extracted with ethyl acetate (120, 60 and 30 ml.). The combined ethyl acetate extract was washed with water (60 ml.), dried (MgSO$_4$) and evaporated to a pale yellow foam (1.10 g.) Trituration with ether containing a few drops of methanol gave the title acid as an off-white solid (0.63 g. 58%), m.p. 146° to 151°, $[\alpha]_D^{23} + 122°$ (c 1.08; (Me$_2$SO), $\lambda_{max.}$ (0.1M pH6 phosphate) 261 nm ($\epsilon$ 9,430), inflexions at 265 nm ($\epsilon$ 9,300) and 272.5 nm ($\epsilon$ 7,250), $\nu_{max.}$ (CHBr$_3$) 3417 (NH), 3600 to 2400 (bonded OH), 1785 (azetidin-2-one), 1738 (dimeric CO$_2$H) and 1694 and 1521 cm$^{-1}$(CONH), $\tau$ (Me$_2$SO-d$_6$) 0.97 (1H, d, J 8.5 Hz; NH), 2.67 and 3.01 (2H and 3H, two m; C$_6$H$_5$O), 4.36 (1H, dd, J 8.5 and 4.5 Hz;

C$_7$-H), 4.91 (1H, d, J 4.5 Hz; C$_6$-H), 5.37 (2H, s; C$_6$H$_5$OCH$_2$), 6.48 (2H, s; C$_2$-H$_2$), 7.4 to 7.9 (2H, partly obscured AB-part of ABX$_3$-system; C$_3$-CH$_2$CH$_3$), 8.93 (3H, t, J 7 Hz; CH$_2$CH$_3$) (Found: C, 55.9, 56.1; H, 5.1, 5.1; N, 7.7, 7.7; S, 8.85. C$_{17}$H$_{18}$N$_2$O$_5$S (362.4) requires C, 56.3; H, 5.0; N, 7.7; S, 8.85%). R$_p$ (system C) 2.47.

EXAMPLE 6 a. t-Butyl 7β-Amino-3-ethylceph-3-em-4-carboxylate

A solution of t-butyl 3-ethyl-7β-phenoxyacetamidoceph-3-em-4-carboxylate (1.0 g. 2.4 mmole) in dry methylene chloride (5 ml.) was added to phosphorus pentachloride (750 mg, 3.6 mmole) and pyridine (0.19 ml, 2.35 mmole) in dry methylene chloride (20 ml.) cooled to −20°. The mixture was stirred at −20° for 30 minutes, and 0° for 1 hour and then allowed to warm to ca. 20° over 30 minutes. Dry methanol (10 ml) was added and the mixture was stirred for 15 minutes and diluted with ethyl acetate (100 ml) and water (100 ml.). The organic phase was re-extracted with water (20 ml.), and the combined aqueous phases were treated with solid sodium hydrogen carbonate to adjust the pH to 6.7, and then extracted with ethyl acetate (2 × 30 ml.). The organic extract was dried (MgSO$_4$) and evaporated, and the residue was triturated with ether-petroleum spirit (b.p. 60 to 80°) to give the title amino-ester as off-white crystals (0.27 g, 40%), m.p. 114 to 117°, [α]$_D^{23}$ +71° (C 0.80; CHCl$_3$), λ$_{max.}$(EtOH) 271.5 nm (ε 6,650), ν$_{max.}$ (Nujol) 3420 and 3350 (NH$_2$), 1770 (azetidin-2-one) and 1707 cm$^{-1}$ (CO$_2$R), τ (CDCl$_3$) 5.09 (1H, d, J 5 Hz; C$_6$-H), 5.32 (1H, d, J 5 Hz; C$_7$-H), 6.52 and 6.79 (2H, AB-q, J 18 Hz; C$_2$-H$_2$), 7.43 and 7.83 (2H, AB-part of ABX$_3$-system, J$_{AX}$,J$_{BX}$ 7 Hz, J$_{AB}$ 13 Hz; C$_3$-CH$_2$CH$_3$), 8.19 (2H, s; NH$_2$), 8.47 (9H, s; CO$_2$(CH$_3$)$_3$), 8.88 (3H, t, J 7 Hz; CH$_2$CH$_3$) (Found: C, 54.9, 54.5; H, 7.1, 6.9; N, 10.0, 10.3; S, 11.2. C$_{13}$H$_{20}$N$_2$O$_3$S (284.4) requires C, 54.95; H, 7.1; N, 9.85; S, 11.3%).

b. t-Butyl 3-Ethyl-7β-phenylthioacetamidoceph-3-em-4-carboxylate

A solution of N,N'-dicyclohexylcarbodiimide (620 mg, 3 mmole) in dry methylene chloride (15 ml.) was added to a stirred solution of t-butyl 7β-amino-3-ethylceph-3-em-4-carboxylate (853 mg. 3 mmole) in dry methylene chloride (10 ml.). A solution of phenylthioacetic acid (505 mg. 3 mmole) in dry methylene chloride (10 ml.) was added over 5 minutes to the mixture which was stirred at ca. 20° for 2 hours. A further portion of carbodiimide (124 mg., 0.6 mmole) was added, and the mixture was stirred for a further 30 minutes and filtered from precipitated N,N'-dicyclohexylurea. The filtrate was washed successively with 3% aqueous sodium hydrogen carbonate solution (50 ml.), water (50 ml.), 2N-hydrochloric acid (25 ml.) and water (25 ml.), dried (MgSO$_4$) and evaporated to a yellow oil which was dissolved in ethyl acetate (8 ml.). The solution was cooled, the precipitated dicyclohexylurea was removed by filtration, and the filtrate was evaporated to give the title ester as a pale yellow foam (1.45 g.), [α]$_D^{23}$ + 67° (c 1.05; CHCl$_3$), λ$_{max.}$ (EtOH) 250.5 nm (E$_{1\ cm.}^{1\%}$ 256), contaminated with ca. 15% by weight of N,N'-dicyclohexylurea and/or the corresponding N-acylurea. The infra red (CHBr$_3$) and p.m.r. (CDCl$_3$) spectra of the product were in accord with the assigned structure.

c. 3-ethyl-7β-phenylthioacetamidoceph-3-em-4-carboxylic acid t-Butyl 3-ethyl-7β-phenylthioacetamidoceph-3-em-4-carboxylate (1.34 g.) was treated with trifluoroacetic acid (12 ml.) and anisole (3 ml.) and worked up as in Example 5(b) to give a pale yellow foam (0.92 g.) Trituration with ether containing a few drops of ethyl acetate gave the title acid as an off-white solid (0.73 g, 65% from the product of Example 6(a)), m.p. 128° to 136°, [α]$_D^{23}$ + 117° (c 1.00; Me$_2$SO), λ$_{max.}$(0.1M pH6 phosphate) 248.5 nm (ε 11,500) ν$_{max.}$(CHBr$_3$) 3355 (NH), 1778 (azetidin-2-one), 1729 (dimeric CO$_2$H) and 1679 and 1514 cm.$^{-1}$ (CONH), τ (Me$_2$SO-d$_6$) 0.90 (1H, d, J 8.5 Hz; NH), 2.64 (5H, m; C$_6$H$_5$S), 4.39 (1H, dd, J 8.5 and 5 Hz; C$_7$-H), 4.93 (1H, d, J 5 Hz; C$_6$-H) 6.23 (2H, s; C$_6$H$_5$SCH$_2$), 6.38 and 6.59 (2H, AB-q, J 18 Hz; C$_2$H$_2$), 7.4 to 7.8 (2H, partly obscured AB-part of ABX$_3$-system; C$_3$-CH$_2$CH$_3$), 8.93 (3H, t, J 7 Hz; CH$_2$CH$_3$) (Found: C, 53.7, 53.5; H, 5.0, 4.8; N, 7.3, 7.4; S, 16.5. C$_{17}$H$_{18}$N$_2$O$_4$S$_2$ (378.5) requires C, 54.0; H, 4.8; N, 7.4; S, 16.95%). R$_p$ (system C) 2.64.

EXAMPLE 7 a. t-Butyl 3-Ethyl-7β-phenylglyoxamidoceph-3-em-4-carboxylate

A similar acylation to 6(b) above, but with phenylglyoxylic acid (450 mg., 3 mmole) gave the title ester as a pale yellow foam (1.36 g.), [α]$_D^{23}$ + 64° (c 0.92; CHCl$_3$), λ$_{max.}$(EtOH) 256 nm (E$_{1\ cm.}^{1\%}$ 346), contaminated with ca. 20% by weight of N,N'-dicyclohexylurea and/or the corresponding N-acylurea. The infra-red (CHBr$_3$) and p.m.r. (CDCl$_3$) spectra of the product were in accord with the assigned structure.

b. 3-Ethyl-7β-phenylglyoxamidoceph-3-em-4-carboxylic acid t-Butyl 3-ethyl-7β-phenylglyoxamidoceph-3-em-4-carboxylate (1.26 g.) was treated with trifluoroacetic acid (12 ml.) and anisole (3 ml.) and worked up as in Example 5(b) to give the title acid as a pale yellow foam (0.84 g. 77% from the product of Example 6(a)), [α]$_D^{23}$ + 83.5° (c 0.92; Me$_2$SO), λ$_{max.}$ (0.1M pH6 phosphate) 260 nm (ε 15,250), ν$_{max.}$ (CHBr$_3$) 3393 (NH), 1780 (azetidin-2-one), 1730 and 1675 (dimeric CO$_2$H and PhCO), and 1696 and 1512 cm.$^{-1}$ (CONH), τ (Me$_2$SO—d$_6$) 0.03 (1H, d, J 8 Hz; NH), 2.0 and 2.3 (5H, two m; C$_6$H$_5$CO), 4.22 (1H, dd, J 8 and 4.5 Hz; C$_7$-H), 4.77 (1H, d, J 4.5 Hz; C$_6$-H), 6.45 (2H, s; C$_2$-H$_2$), ca. 7.6 (2H, partly obscured AB-part of ABX$_3$-system; C$_3$—CH$_2$CH$_3$), 8.92 (3H, t, J 7 Hz; CH$_2$CH$_3$) (Found: C, 55.3; H, 4.8; N, 7.4; S, 8.0. C$_{17}$H$_{16}$N$_2$O$_5$S (360.4) requires C, 56.7; H, 4.5; N, 7.8; S, 8.9%). R$_p$ (system C) 2.87.

EXAMPLE 8 t,Butyl 7β-Cyanoacetamido-3-ethylceph-3-em-4-carboxylate

A similar acylation to 6(b) above, but with cyanoacetic acid (255 mg., 3 mmole) gave the title ester as a yellow gel (1.19 g.), [α]$_D^{23}$ + 74° (c 0.97; CHCl$_3$), λ$_{max.}$ EtOH) 266 nm (E$_{1\ cm.}^{1\%}$ 177), contaminated with 15 to 20% by weight of N,N'-dicyclohexylurea and/or the corresponding N-acylurea. The infra-red (CHBr$_3$) and p.m.r. (CDCl$_3$) spectra of the product were in accord with the assigned structure.

EXAMPLE 9 a. 7β-Amino-3-ethylceph-3-em-4-carboxylic Acid

Trifluoroacetic acid (12 ml.) was added to a solution of t-butyl 7β-amino-3-ethylceph-3-em-4-carboxylate (924 mg. 3.25 mmole) in anisole (3 ml.). The solution was stirred at ca. 20° for 10 minutes and the solvents were evaporated in vacuo. Water (5 ml.) was added to the residue when a solid remained out of solution. The supernatant liquors were decanted and the solid was washed by decantation with ether (2 × 3 ml.), washed with water (5 ml.), filtered and dried to give the title aminoacid (272 mg. 37%), τ (Me$_3$SO—d$_6$) 4.3 (broad signal; NH$_3$$^+$and H$_2$O), 5.01 (1H, d, J 5 Hz.) and 5.23 (1H, d, J 5 Hz.) (C$_6$—H and C$_7$—H), 6.47 (2H, s; C$_2$—H$_2$), 7.6 (2H, partly obscured AB-part of ABX$_3$-system; C$_3$-CH$_2$CH$_3$), 8.89 (3H, t, J 7 Hz; CH$_2$CH$_3$). The decanted aqueous solution was adjusted to pH 3.5 with triethylamine and cooled to give a second crop of the title amino-acid (294 mg. 40%).

b. 7β-Cyanoacetamido-3-ethylceph-3-em-4-carboxylic Acid

Hexamethyldisilazane (1.4 ml., 7.44 mmole) was added to a suspension of 7β-amino-3-ethylceph-3-em-4-carboxylic acid (566 mg., 2.48 mmole) in dry 1,2-dichloroethane (15 ml.), and the mixture was heated under reflux for 1¾ hours with exclusion of moisture. The solvent was removed in vacuo and the residual brown oil was dissolved in dry ethyl acetate (ca. 4 ml.) and stirred while a solution of cyanoacetyl chloride (308 mg., 2.98 mmole) in dry ethyl acetate (2ml.) was added. The mixture was stirred at ca. 20° overnight and then evaporated. trituration of the residue with methanol-ether gave the title acid (445 mg., 61%), m.p. 185° to 191° (dec.), [α]$_D$ + 140° (c 1.11; Me$_2$SO), λ$_{max.}$ (0.1M pH6 phosphate) 262 nm (ε 8,050), ν$_{max.}$ (Nujol) 3262 (NH), 2264 (CN), 1759 (azetidin-2-one), 1712 (dimeric CO$_2$H) and 1651 and 1531 cm.$^{-1}$ (CONH), τ (Me$_2$SO-d$_6$) 0.83 (1H, d, J 8 Hz; NH), 4.38 (1H, dd, J 8 and 4.5 Hz; C$_7$—H), 4.89 (1H, d, J 4.5 Hz; C$_6$—H), 6.23 (2H, s; CH$_2$CN), 6.36 and 6.58 (2H, AB-q, J 18 Hz; C$_2$—H$_2$), 7.4 to 7.9 (2H, partly obscured AB-part of ABX$_3$-system, C$_3$—CH$_2$CH$_3$), 8.93 (3H, t, J 7 Hz; CH$_2$CH$_3$) (Found: C, 48.5; H, 4.5; N, 14.3; S, 10.6. C$_{12}$H$_{13}$N$_3$O$_4$S (294.9) requires C, 48.8; H, 4.4; N, 14.2; S, 10.9%). R$_p$ (system C) 0.31.

EXAMPLE 10 t-Butyl 7β-(2-t-Butoxycarbonylamino-2-phenylacetamido)-3-ethylceph-3-em-4-carboxylate Hydrogen was bubbled through a suspension of 10%-palladium on carbon (151 mg., ca. 0.14 mmole) in pure tetrahydrofuran (2 ml.) for 5 minutes. A solution of t-butyl 7β-(2-t-butoxycarbonylamino-2-phenylacetamido)-3-vinyl ceph-3-em-4-carboxylate (60 mg., ca. 0.11 mmole) in tetrahydrofuran (2 ml.) was added and the mixture stirred in a hydrogen stream for 3½ hours (after this time the characteristic vinyl absorption at 295 nm. in the ultraviolet, had disappeared). The system was flushed with nitrogen and the catalyst removed by filtration of the suspension through a bed of kieselguhr. The solvent was removed in vacuo to give the crude ethyl derivative (30 mg.), [α]$_D$$^{20}$ + 3.25° (c 1.8, CHCl$_3$), λ$_{max.}$ (CHCl$_3$) 266.5 nm. (ε 5,490) ν$_{max.}$ (CHBr$_3$) 3350(NH), 1760 (β-lactam), 1700 (CO$_2$R), and 1680 and 1500 (CONH) cm.$^{-1}$ τ (CDCl$_3$) 2.64 (Ph), 3.04 (CONH, d, J 9 Hz.), 4.23 (CHNH, d, J 7 Hz.), 4.28 (C$_{(7)}$—H, dd, J 4.5 and 9 Hz.), 4.76 (CHNH, d, J 7 Hz.), 5.09 (C$_{(6)}$—H,d, J 4.5 Hz.), 6.62 and 6.88 (C$_{(2)}$—CH$_2$, AB-q, J$_{AB}$ 18 Hz.), 7.3–8.0 (CH$_2$CH$_3$ complex), 8.46 and 8.59 (t-butyl), and 8.9 (CH$_2$CH$_3$).

EXAMPLE 11 a. Diphenylmethyl 7β-amino-3-(2-cyanoethyl)ceph-3-em-4-carboxylate

A suspension of phosphorus pentachloride (606 mg., ca 2.9 mmole) in methylene dichloride (5 ml) was warmed until most of the phosphorus pentachloride had dissolved. A solution of pyridine in methylene dichloride (4.6 ml., as a 10% v/v solution, ca 5.7 mmole) was added, and the mixture cooled to 0°. A solution of diphenylmethyl 3-(2-cyanoethyl)-7β-(2-thienylacetamido)ceph-3-em-4-carboxylate (700 mg ca 1.3 mmole) in methylene dichloride (9 ml) was added and the mixture was stirred at 0° for 30 minutes. After a further 30 minutes at 25° the solution was run into a vigorously stirred mixture of methanol (2 ml.) and methylene dichloride (10 ml). the resulting solution was washed with dilute aqueous sodium bicarbonate solution and water, and dried and evaporated in vacuo the residue was triturated with petroleum to remove traces of pyridine and the resulting solid (500 mg) dissolved in ethyl acetate. The solvent was removed in vacuo and the residue washed with ether to give the title compound (450 mg) as small needles m.p. 118° to 122° (decomp) [α]$_D$$^{25}$ 49.1° (c 1.3, CHCl$_3$) λ$_{max.\ (CHCl3)}$ 258.5 nm (ε 5,950) ν$_{max.}$ (CHBr$_3$) 3450 and 3380 (NH$_2$), 1780 (β-lactam) 1728 CO$_2$R) and 758 and 740 (CHPh$_2$) cm.$^{-1}$ τ (CDCl$_3$) 2.62 (Ph), 3.05 (CHPh$_2$) 5.06 and 5.23 (C6 and C7 —H, two doublets J 5 Hz.) 6.48 and 6.65 (C2 —CH$_2$ AB-quartet, J 18 Hz.) 7.1 to 7.6 (CH$_2$CH$_2$CN complex) 7.5 (NH$_2$). The compound ran to the cathode on electrophoresis at pH 1.9 b. Diphenylmethyl 7β-(D-2-t-Butoxycarboxylamino-2-phenylacetamido)-3-(2-cyanoethyl)ceph-3-em-4-carboxylate A solution of D-2-t-butoxycarbonylamino-2-phenylacetic acid(275 mg ca 1.1 mmole) in N,N-dimethyl-formamide (2.5 ml) was added over 10 minutes at 25° to a solution of diphenylmethyl 7β-amino-3-(2-cyanoethyl) ceph-3-em-4-carboxylate (360 ca 0.85 mmole) and dicyclohexylcarbodiimide (253.5 mg ca 1.1 mmole) in methylene dichloride (10 ml) the mixture was stirred at 25° for 30 minutes and filtered. The filtrate was washed with water, and dried and evaporated in vacuo the residue in benzene:ethyl acetate = 1:1 was filtered through a short column of Merck kieselgel and the solvent evaporated in vacuo to give the title compound (550 mg) as a froth [α]$_D$$^{23}$ – 61.2° (c 1.1, CHCl$_3$), λ$_{max.}$ (CHCl$_3$) 258.5 nm. (ε 5.750) ν$_{max.}$ (CHBr$_3$) 3400 and 3480 (NH) 1796 (β-lactum)1720 (CO$_2$R) 1710 and 1502 (NHCO$_2$R) 1680 and 1520 (CONH) and 2.64 756 and 740 (CHPh$_2$) cm.$^{-1}$ ε (CDCL$_3$) 3.64 (Ph) 2.92 (NH, doublet J 9 Hz.), 3.11 (CHPh$_2$) 4.18 (C 7-H double doublet, J 5 and 9 Hz.) 4.27 (CHNH, doublet J 7 Hz), 4.73 (CHNH, doublet J 7 Hz), 5.11 (C6-H doublet J 5 Hz.) 6.56 and 6.78 (C2-CH$_2$ AB-quartet J$_{AB}$ 18 Hz.), ca 7.3 to 7.7 (CH$_2$CH$_2$CN, complet) and 8.58 (t-butyl).

c. 7β-(D-2-Amino-2-Phenylacetamido)-3-(2-cyanoethyl) ceph-3-em-4-carboxylic acid Trifluoroacetic Acid Salt.

A solution of diphenylmethyl-7β-(D-2-t-butoxycarbonylamino-2-phenylacetamido)-3-(2-cyanoethyl) ceph-3-em-4-carboxylate (500 mg) in trifluoroacetic acid (2.5 ml) was kept at 23° for 5 minutes. The trifluoroacetic acid was removed in vacuo and the residue partitioned between ethyl acetate and dilute aqueous trifluoroacetic acid. The aqueous phase was washed with ether and after removal of traces of ether in vacuo, freeze dried to give the title compound (300 mg) as an amorphous solid m.p. 80 to 83° $[\alpha]_D^{23}$ + 46.8° (c 1.1 MeOH) $\lambda_{max}$. (0.1M pH 6 phosphate buffer) 261 nm ($\epsilon$ 7,050) $\nu_{max}$. (Nujol) ca 3200 (NH), c 2600 to 2700 ($NH_3^+$) 2250 (CN) 1768 (β-lactam 1690 ($CO_2H$), 1670 and 1520 (CONH) and ca 1540 ($CF_3CO_2^-$) τ ($CF_3CO_2H$) ca 2.18 ($NH_3^+$), 2.4 (Ph) 4.14 ($C_7$-H, double doublet J 5 and 8 Hz), 4.45 ($CHNH_3$ ill resolved quartet) 4.74 ($C_6$-H doublet J 5 Hz), 6.30 and 6.52 ($C_2$-$CH_2$ AB-quartet $J_{AB}$ 18 Hz.) and ca 6.7 and ca 7.1 ($CH_2CH_2CN$ complex). The compound ran to the cathode on electrophoresis at pH 1.9.

APPENDIX

The starting material for Example 4(a) was prepared by the following series of reactions.

a. [4-Diphenylmethoxycarbonyl-7β-(2-thienylacetamido)ceph3-em-3-ylmethyl]-triphenylphosphonium iodide A solution of diphenylmethyl 3-iodomethyl-7β-(2-thienylacetamido)ceph-3-em-4-carboxylate (30 g.,) Rf 0.6 in ethyl acetate (500 ml.) was stirred in the dark at room temperature and treated, over 45 minutes, with a solution of triphenylphosphine (24.9 g., ca. 2 equivs.) in ethyl acetate (150 ml.). The mixture was stirred for a further 60 minutes at 0°, and the precipitated solid collected by filtration. The solid was washed with ethyl acetate and dried in vacuo to give the phosphonium iodide (31.7 g., 74.5%), Rf 0.0, m.p. 142°–146° (decomp.), $[\alpha]_D$ + 10° (tetrahydrofuran), $\lambda_{max}$ 269 nm ($\epsilon$ 9,400) and 276 nm ($\epsilon$ 8,600) $\nu_{max}$ (CHBr$_3$) 3350 (NH), 1780 (β-lactam), 1710 ($CO_2R$), 1680 and 1505 (CONH), and 1445 (P-C(aryl)) cm$^{-1}$, τ (CDCl$_3$) 4.39 ($C_{(7)}$-H,dd,J4.5 and 9 Hz), 5.19 ($C_{(6)}$—H, d, J 4.5 Hz) 4.75 and 4.85 ($\underline{CH}_2$-P, four major signals of two AB-q $J_{P-H}$ 16 Hz), 6.05 and 6.68 ($C_{(2)}$ — $CH_2$ two dd, $J_H$—$_H$ 18 Hz, $J_{P-H}$ 3–4 Hz). [Found: C, 59.3; H, 4.5; I, 13.4; N, 2.6; P, 3.4; S, 7.3. $C_{45}H_{38}IN_2O_4PS_2$ (892.8) requires C, 60.5; H, 4.3; I, 14.2; N, 3.1; P, 3.5; S, 7.2%].

b. Diphenylmethyl 7β-(2-thienylacetamido)-3-(triphenylphosphoranylidene-methyl) ceph-3-em-4-carboxylate A solution of [4-diphenylmethoxycarbonyl-7β-(2-thienylacetamido) ceph-3-em-3-ylmethyl] triphenylphosphonium iodide (25 g.) in acetone (300 ml.) with water (40 ml.) was cooled to 0° and taken to pH 11 with 2Nsodium hydroxide. The mixture, containing a precipitated yellow soid, was diluted with acetone (200 ml.) and water (50 ml.), and filtered. The collected solid was washed with acetone and ether, and dried in vacuo to give diphenylmethyl 7β-(2-thienylacetamido)-3-(triphenylphosphoranylidenemethyl) ceph-3-em-4-carboxylate (17 g., 78.5%) as a yellow crystalline solid, m.p. 133°-138° (Decomp), $[\alpha]_D$ — 35°(CHCl$_3$), $\lambda_{max}$ (CHCl$_3$) 388 nm. ($\epsilon$ 18,500), 273 nm ($\epsilon$ 6,240) and 267 nm ($\nu$ 6,940), $\nu_{max}$ (CHBr$_3$) 3360 (NH), 1746 (β-lactam), 1670 ($CO_2R$), 1642 and 1500 (CONH), and 1438 (P-C aryl) cm$^{-1}$; τ (CDCl$_3$) 4.82 ($C_{(7)}$-H, dd, J 4.5, 9Hz), 4.95 ($C_{(6)}$—H, d, J 4.5 Hz), 7.11 and 7.55 ($C_{(2)}$—$CH_2$, two dd. $J_{H-H}$14Hz., $J_{P-H}$ 1–2 Hz) and 4.5

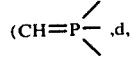

$J_{P-H}$ 22 Hz). [Found: C, 66.6; H, 4.7, N, 2.9; P, 3.9; S, 7.8. $C_{45}H_{37}N_2O_4S_2P$ (764.8) requires C, 70.6; H, 4.8; N, 3.6; P, 4.0; S, 8.4%]

c. Diphenylmethyl 7β-(2-thienylacetamido)-3-vinyl ceph-3-em-4-carboxylate

A solution of diphenylmethyl 7β-(2-thienylacetamido)-3-(triphenylphosphoranylidenemethyl) ceph-3-em-4-carboxylate (2.55 g.) Rf 0.0, in methylene dichloride (150 ml.) was treated, at 10°, with 40% formaldehyde solution (20 ml.). The mixture was stirred vigorously at 10° until the orange colour characteristic of the starting material had disappeared (ca 30 minutes). The methylene chloride solution was dried and evaporated in vacuo. The residue was triturated with ethyl acetate and the insoluble crystalline material collected by filtration. The filtrate, on treatment with ether, gave a further crop of crystalline material. The combined solids (1.25 g., 72.5%) were crystallized from methanol to give pure diphenylmethyl 7β-(2-thienylacetamido)-3-vinylceph-3-em-4-carboxylate (780 mg.), Rf 0.5, as small needles, m.p. 176 to 177° (dec) $[\alpha]_D$ — 132.8°(CHCl$_3$), $\lambda_{max}$ 296 nm ($\epsilon$ 13,620) $\nu_{max}$ (CHBr$_3$) 3420 (NH), 1788 (β-lactam), 1720 ($CO_2R$), and 1680 and 1510 (CONH) cm$^{-1}$; τ (CDCl$_3$) 4.21 ($C_{(7)}$—H, dd, J 4.5 and 9 Hz), 5.06 ($C_{(6)}$—H, d, J 4.5 Hz), 6.36 and 6.58 ($C_{(2)}$—$CH_2AB$-q, $J_{AB}$18 Hz), and 3.2 (dd), 4.65 (d) and 4.8 (d) (—CH = CH$_2$). ABX system, $J_{AX}$ 16 Hz., $J_{BX}$ 12 Hz., $J_{AB}$ 0 Hz). [Found: C, 64.9; H, 4.8; N, 5.3; S, 12.4. $C_{28}H_{24}N_2O_4S_2$ (516.5) requires C, 65.1; H, 4.7; N, 5.4; S, 12.4%].

d. Diphenylmethyl 7β-amino-3-vinylceph-3-em-4-carboxylate

A suspension of phosphorus pentachloride (4.71 g., 22.5 mmole) in methylene dichloride (35 ml.) was warmed until most of the phosphorus pentachloride had dissolved. A solution of pyridine in methylene dichloride (18.2 ml., as a 10% v:v solution, ca 22.5 mmole pyridine) was added, and the white suspension was warmed to 23° for 10 minutes, then cooled to 0°. A solution of diphenylmethyl 7β-(2-thienylacetamido)-3-vinylceph-3-em-4-carboxylate (5.16 g., 10 mmole) in methylene dichloride (70 ml.), cooled to 0°, was added and the mixture stirred for 20 minutes. The solution was run into a vigorously stirred mixture of methanol (10 ml.) in methylene dichloride (50 ml.) and the resulting solution washed with aqueous sodium bicarbonate and water, and dried and evaporated in vacuo. The residual gum, in a small volume of chlorogorm, was run onto a column (7 × 4 cm.) of Kieselgel (0.02 to 0.5 mm.), and the column eluted with chloroform (2 × 100 ml.), then chloroform:ethyl acetate = 1 : 1 (3 × 100 ml.). The first chloroform fraction and the last chloroform : ethyl acetate fraction were discarded and the other fractions combined and evaporated in vacuo. The residue was triturated with ether to give the amino (2.7 g., 69%) as small needles, m.p. 157°–160° (decomp), $[\alpha]_D$ — 155.4° (CHCl$_3$), $\lambda_{max}$. 296.5 nm. ($\epsilon$, 12,400), $\nu_{max}$. (CHBr$_3$) 3460 and 3390 (NH), 1780 ($\beta$-lactam), 1730 (CO$_2$R) and 910 cm.$^{-1}$ (CH=CH$_2$), $\tau$ (CDCl$_3$) 2.65 (Ph), 3.02 (C$\underline{H}$ Ph$_2$), 3.09 (CH=CH$_2$, $dd$, J 11 and 18 Hz.), 4.64 and 4.82 (C$\underline{H}$=CH$_2$, two d, J 18 and 11 Hz. resp.), 5.09 (C$_{(7)}$—H, $d$, J 5 Hz.), 5.32 (C$_{(6)}$—H, $d$, J 5 Hz.)., 6.35 and 6.85 (C$_{(2)}$—CH$_2$, AB-q J 18 Hz), and 8.21 (NH$_2$); (DMSO-d$_6$) 2.60 (Ph), 3.03 (C$\underline{H}$ Ph$_2$), 3.28 (C$\underline{H}$ = CH$_2$, $dd$ J 11 and 17 Hz.), 4.40 and 4.76 (CH=C$\underline{H}_2$, two $d$, J 17 and 11 Hz. resp.), 4.91 (C$_{(7)}$-H, $d$, J 5 Hz.), 5.12 (C$_{(6)}$—H, $d$, J 5 Hz), 6.09 and 6.45 (C$_{(2)}$—CH$_2$, AB-q J 18 Hz.) and 7.62 (NH$_2$) (Found: C, 66.2; H, 5.1; N, 6.8; S, 8.1. C$_{22}$H$_{20}$N$_2$O$_3$S requires C, 67.3; , H, 5.15; N, 7.15; S, 8.2%).

e. Diphenylmethyl 7$\beta$-(D-2-t-butoxycarbonylamino-2-phenylacetamido)-3-vinylceph-3-em-4-carboxylate A solution of diphenylmethyl 7$\beta$-amino-3-vinylceph-3-em-4-carboxylate (1.57 g., 4 mmole) in methylene dichloride (25 ml.) with dicyclohexylcarbodiimide (907 mg., 4.4 mmole) was treated slowly (over 10 minutes) with a solution of D-2-t-butoxycarbonylamino-2-phenylacetic acid (1.1 g., 4.4 mmole) in N,N-dimethylformamide (10 ml.). The mixture was stirred at 23° for 30 minutes and dicyclohexylurea removed by filtration. The filtrate was washed with water and dried and evaporated in vacuo to give a pale yellow solid. This material was crystallised from methanol, and the isolated material washed with ether, to give the crude title compound (2.2 g.) (contaminated with dicyclohexylurea). The crude compound in benzene methyl acetate (2:5) was filtered through a short column of Kieselgel 0.02 –0.5 mm., 10 cm. × 2.5 cm.). Evaporation of the solvent in vacuo and washing the crystalline residue with ether gave the pure title compound (1.6 g., 64%) as small needles m.p. 200°–202°, $[\alpha]_D$ — 129° (CHCl$_3$), $\xi_{max}$ 294.5 nm. ($\epsilon$ 14,400), $\lambda_{max}$. 3395 (NH), 1780 ($\beta$-latam), 1712 (CO$_2$R), 1690 and 1500 (CONH) and 912 cm.$^{-1}$ (CH=CH$_2$),$\tau$(CDCl$_3$) 3.05 (CHPh$_2$),3.03 (C$\underline{H}$=CH$_2$, $dd$, J 17 and 11 Hz). 3.08 (NH, $d$, J 9 Hz) 4.23 (C$_{(7)}$—H, $dd$, J 9 and 4.5 Hz), 4.28 (CH-N$\underline{H}$, $d$, J 7 Hz), 4.65 and 4.79 (CH=C$\underline{H}_2$, two $d$, J 17 and 11 Hz resp.), 4.77 (C$\underline{H}$-NH, $d$, J 7 Hz), 5.10 (C$_{(6)}$—H, $d$, J 4.5 Hz), 6.46 and 6.70 (c$_{(2)}$—CH, AB-q, J 18 Hz) 8.58 (C[CH$_3$]$_3$). (Found: C, 66.6; H, 5.6; N, 6.4; S, 5.1. C$_{35}$H$_{35}$N$_3$O$_6$S requires C, 67.2; H, 5.65; N, 6.7; S, 5.1%).

Biological results are given in the following table:

Pharmaceutical Example

| Tablet | | |
|---|---|---|
| a) | 7$\beta$-(D-2-amino-2-phenylacetamido)-3-ethyl-ceph-3-em-4-carboxylic acid | 70 mg. |
| b) | Mannitol | 21 mg. |
| c) | Potato Starch | 12.9 mg. |
| d) | Maize Starch | 7 mg. |
| e) | Magnesium stearate | 1.1 mg. |

The dry ingredients (a), (b) and (c) were blended together and granulated with a 10% aqueous paste of (d). The granules were dried and lubricated by blending in (e) and compressed on suitable punches. The tablets may be coated if required, for instance with a readily soluble conventional film coating.

I claim:
1. A cephalosporin antibiotic of the formula:

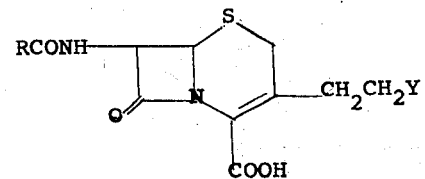

wherein:
Y is hydrogen or cyano and
R is phenoxymethyl; phenylthiomethyl; phenylcarbonyl; cyanomethyl or the group

in which R$^6$ is thien-2-yl; thien-3-yl; phenyl or phenyl substituted with halo, hydroxy, lower alkyl, nitro, amino, lower alkanoyl, lower alkoxy or lower alkylmercapto and X$^1$ is hydrogen, amino, hydroxy or carboxyl; or a physiologically acceptable salt thereof.

2. A cephalosporin antibiotic as claimed in claim 1 wherein R is

3. A compound as claimed in claim 2 wherein R$^6$ is thien-2-yl or thien-3-yl.

|  | Tube Dilution Assay ($\gamma$/ml.) | | | | | | | | Mouse Protection (ED$50$/mg/Kg/dose) |
|---|---|---|---|---|---|---|---|---|---|
|  | Gram Positive | | | | Gram Negative | | | | |
| Compound of Example | STAPH AUREUS 604 | STAPH AUREUS 663 | STAPH AUREUS 3452 | STAPH AUREUS 11127 | E. COLI 573 | S. TYPHIMURIUM 804 | PR. MIRABILIS 431 | STAPH AUREUS 11127 | *R.O.U.R. |
| 1(d) | 1.6 | 0.3 | 1.6 | 0.08 | 8 | 16 | 16 | <6 | 45 |
| 2(c) | 1.25 | 0.08 | 4 | 1 | 62 | 16 | 31 |  | 2.1 |

*R.O.U.R. = % recovery of the antibiotic from the urine of female rats following oral administration of the antibiotic.

4. The compound of claim 1 which is 7β-(D-2-amino-2-phenylacetamido)-3-ethylceph-3-em-4-carboxylic acid.

5. The compound of claim 1 which is 7β-(D-2-amino-2-phenylacetamido)-3-(2-cyanoethyl)ceph-3-em-4-carboxylic acid.

6. The compound of claim 1 which is 3-(2-cyanoethyl)-7β-(2-thienylacetamido)ceph-3-em-4-carboxylic acid.

7. The compound of claim 1 which is 3-ethyl-7β-(2-thienylacetamido)ceph-3-em-4-carboxylic acid.

8. The compound of claim 1 which is 3-ethyl-7β-phenoxyacetamidoceph-3-em-4-carboxylic acid.

9. The compound of claim 1 which is 3-ethyl-7β-phenylthioacetamidoceph-3-em-4-carboxylic acid.

10. The compound of claim 1 which is 3-ethyl-7β-phenylglyoxamidoceph-3-em-4-carboxylic acid.

11. The compound of claim 1 which is 7β-cyanoacetamido-3-ethylceph-3-em-4-carboxylic acid.

* * * * *